(12) United States Patent
John et al.

(10) Patent No.: US 8,002,701 B2
(45) Date of Patent: Aug. 23, 2011

(54) MEDICAL ALARM AND COMMUNICATION SYSTEM AND METHODS

(75) Inventors: Michael Sasha John, Larchmont, NY (US); David R. Fischell, Fair Haven, NJ (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 0 days.

(21) Appl. No.: 11/684,801

(22) Filed: Mar. 12, 2007

(65) Prior Publication Data

US 2007/0213600 A1  Sep. 13, 2007

Related U.S. Application Data

(60) Provisional application No. 60/767,212, filed on Mar. 10, 2006, provisional application No. 60/830,133, filed on Jul. 12, 2006.

(51) Int. Cl.
*A61B 5/04* (2006.01)
*A61N 1/08* (2006.01)
(52) U.S. Cl. ............ 600/300; 607/60; 128/903
(58) Field of Classification Search .......... 600/300, 600/301
See application file for complete search history.

(56) References Cited

U.S. PATENT DOCUMENTS

| 3,867,950 A | 2/1975 | Fischell |
| 3,888,260 A | 6/1975 | Fischell |
| 4,003,379 A | 1/1977 | Ellinwood, Jr. |
| 4,223,678 A | 9/1980 | Langer et al. |
| 4,295,474 A | 10/1981 | Fischell |
| 4,373,527 A | 2/1983 | Fischell |
| 4,543,955 A | 10/1985 | Schroeppel |
| 4,658,830 A | 4/1987 | Sarnoff |
| 4,796,641 A | 1/1989 | Mills et al. |
| 4,905,707 A | 3/1990 | Davies et al. |
| 5,042,497 A | 8/1991 | Shapland |
| 5,113,869 A | 5/1992 | Nappholz et al. |
| 5,135,004 A | 8/1992 | Adams et al. |
| 5,139,028 A | 8/1992 | Steinhaus et al. |
| 5,305,745 A | 4/1994 | Zacouto |
| 5,313,953 A | 5/1994 | Yomtov et al. |
| 5,330,505 A | 7/1994 | Cohen |
| 5,402,794 A | 4/1995 | Wahlstrand et al. |
| 5,404,877 A | 4/1995 | Nolan et al. |
| 5,409,009 A | 4/1995 | Olson |

(Continued)

OTHER PUBLICATIONS

Warnecke, H., et al., "Clinical Heart Transplantation without Routine Endomycardial Biopsy", The Journal of Heart and Lung Transplantation, vol. 11, No. 6, Nov./Dec. 1992, pp. 1093-1102.

(Continued)

*Primary Examiner* — Eric F Winakur
*Assistant Examiner* — Bobby Soriano
(74) *Attorney, Agent, or Firm* — Rosenberg, Klein & Lee

(57) ABSTRACT

A medical alarm communications system comprises a pager like device to be kept near a patient. The pager like device communicates medical alerts regarding the patient to a remote central station, which can provide therapeutic and/or diagnostic assistance by communicating to the pager like device. When the pager like device determines that an alert should be sent to the central station, it attempts to establish communication with the central station according to a primary communication protocol. If this attempt is unsuccessful according to some predetermined criteria (e.g. too much time has elapsed before communication is established), then the pager like device generates a message to the patient indicative of the failure, and The attempts to establish communication with the central station according to a secondary communication protocol.

15 Claims, 8 Drawing Sheets

U.S. PATENT DOCUMENTS

| | | |
|---|---|---|
| 5,411,031 A | 5/1995 | Yomtov |
| 5,417,717 A | 5/1995 | Salo et al. |
| 5,496,351 A | 3/1996 | Plicchi et al. |
| 5,497,780 A | 3/1996 | Zehender |
| 5,531,768 A | 7/1996 | Alferness |
| 5,730,125 A | 3/1998 | Prutchi et al. |
| 5,792,066 A | 8/1998 | Kwong |
| 5,800,498 A | 9/1998 | Obino et al. |
| 5,876,353 A | 3/1999 | Riff |
| 6,112,116 A | 8/2000 | Fischell et al. |
| 6,128,526 A | 10/2000 | Stadler et al. |
| 6,230,049 B1 | 5/2001 | Fischell et al. |
| 6,272,379 B1 | 8/2001 | Fischell et al. |
| 6,368,284 B1 | 4/2002 | Bardy |
| 6,468,263 B1 | 10/2002 | Fischell et al. |
| 6,501,983 B1 | 12/2002 | Natarajanl et al. |
| 6,609,023 B1 | 8/2003 | Fischell et al. |
| 6,741,885 B1 | 5/2004 | Park et al. |
| 6,804,555 B2 | 10/2004 | Warkentin |
| 6,980,851 B2 | 12/2005 | Zhu et al. |
| 6,985,771 B2 | 1/2006 | Fischell et al. |
| 7,054,679 B2 | 5/2006 | Hirsh |
| 2002/0013518 A1* | 1/2002 | West et al. .......... 600/300 |
| 2003/0083582 A1 | 5/2003 | Hirsh |
| 2003/0149423 A1 | 8/2003 | Fischell et al. |
| 2004/0059238 A1 | 3/2004 | Fischell et al. |
| 2004/0116981 A1* | 6/2004 | Mazar .................. 607/60 |
| 2005/0113705 A1 | 5/2005 | Fischell et al. |
| 2005/0177049 A1 | 8/2005 | Hardahl et al. |
| 2006/0064136 A1 | 3/2006 | Wang |
| 2007/0112982 A1* | 5/2007 | Sichner et al. .......... 710/100 |

OTHER PUBLICATIONS

Knosalla, C., et al., "Intramyocardial Electrogram Recordings (IMEG) for Diagnosis of Cellular and Humoral Mediated Cardiac Allograft Rejection", Annals of Thoracic and Cardiovascular Surgery (ATCS), vol. 6, No. 2, 2000, pp. 89-94.

* cited by examiner

MEDICAL ALARM AND COMMUNICATION SYSTEM AND METHODS

REFERENCE TO RELATED APPLICATIONS

This application claims priority of provisional patent application No. 60/767,212 filed Mar. 10, 2006 to John, entitled Medical Alarm and Communication System and Methods as well as provisional application No. 60/830,133 entitled "Systems and Strategies for Long-Term Monitoring of Cardiac Status" filed on Jul. 12, 2006, to John et al.

BACKGROUND OF THE INVENTION

1. Field of the Invention

The invention is in the field of medical monitoring devices which monitor and assess patient medical conditions and provide patient alerting when relevant medical events are detected.

A growing number of medical monitoring, storage, and alerting systems have evolved to assist in providing modern medical treatments. These systems can alert a patient when medically significant events occur in order to enable adequate intervention in the treatment or amelioration of disorders and their symptoms. These events can simply be times at which a patient is scheduled to take medication, or can be events which are detected by an implanted device, such as an electrical stimulator or drug pump, which is configured to sense biological activity and to detect the occurrence of medically relevant abnormalities. One area in which these devices are beginning to play a central role is in the treatment of neurological and cardiac disorders. The ability to monitor, detect, and predict cardiac abnormalities related to, for example, ischemia can decrease the fatalities related to these disorders. In response to such detection patients may be provided with sufficient prior warning to allow them to obtain treatment or other intervention before having a fatal heart attack.

2. Prior Art

In U.S. Pat. Nos. 6,112,116, 6,272,379, 6,468,263, 6,609,023 and 6,985,771 Fischell et al describe such systems for acute detection and warning, as well as for communication between an implanted device and a central diagnostic station, however, these do not describe capabilities related to increasing the efficiency, reliability, and utility of communication between the patient, the implanted device, an external patient device, local bystanders, emergency medical personnel, a physician, a translator, and the central diagnostic station. Other relevant prior art are U.S. Pat. Nos. 6,980,851 6,741,885 and US applications 2005/0177049, 2003/0083582 and 2003/0004548, which describe measurement and storage of cardiac data, and also describe providing alarms in response to detection of abnormal events.

Fischell et al., in US Patent Application 2005/0113705, describe a Cardiotracker system which allows for extended recording of cardiac data. John et al, in U.S. patent application Ser. No. 2007/0208263, entitled 'Systems and Methods of Medical Monitoring According to Patient State' describes a CardioTrend system. This application supplements these two other applications.

Advanced warning systems (AWSs) offer a number of features which are advantageous in dealing with life threatening disorders such as myocardial infarction, stroke, seizure, and syncope. AWSs can provide various types of warnings to a patient. These may be auditory alert signals which are coded temporally tonally, and by volume, and have characteristics which reflect the seriousness and type of medical event which was detected. AWSs, such as those described in 2003/0149423 (the '423 application, to Fischell) allow for communication with a central diagnostic station, where a medical practitioner evaluates the data which have been sent and determines if the patient should be alerted or not. Other advantages are also provided in '423, for example, when an alarm is triggered and data is sent to the central station, the medical practitioner can rapidly and conveniently communicate with the patient over a wireless connection such as a cellular connection, and can utilize a satellite communication/tracking system to localize the patient's location similar to the ONSTAR system available in many modern vehicles. When indicated, the practitioner can rapidly send an emergency medical team (EMT) team coordinates to the patient's location or can relay information to the patient about the location of the nearest hospital.

SUMMARY OF THE INVENTION

The present invention pertains to a medical alarm and communication system (ACS), which includes the systems, services, and methods which are provided both at the location of the patient as well as at a distally located diagnostic center. When the invention is applied to the monitoring of cardiac status it is referred to as the "CardioTrend system."

The ACS may take the form of a portable device configured to alert a patient to a medical emergency and for providing subsequent communication and data transmission to medical practitioners. The ACS achieves this communication using a number of methods and components which can be implemented according to patient/physician preferences or according to the type of medical event which occurs. The ACS may be realized with most, or all, of its components located internally or externally to the patient, depending upon the particular implementation of the invention. In the illustrations and descriptions of the present application, while certain features are described for the implanted components of the ACS, these should be understood to be mostly interchangeable with external components, and modifications to one system can be understood as logically resulting in corresponding changes to the other in order to maintain the utility of the invention.

Rather than simply issuing an alert signal to a patient or the central station, the ACS is further designed to assist an unconscious patient by determining if the patient is unconscious and then alerting and informing bystanders as to the patient's condition. In disorders such as syncope, providing an alert can serve to notify bystanders that a serious medical event has occurred (e.g., the patient is not merely napping on the beach or a park bench, but rather suffering from syncope or experiencing a heart attack), and may instruct them, and provide information, to help the patient. The ACS communicates to people who may be in the vicinity of the patient using audio and visual alarms, including a warning signal such as a siren sound, loud beeping, verbal, and/or audiovisual message.

The ACS is configured to acquire and utilize a number of types of information. In addition to alerting the patient to a potentially relevant medical condition which is detected in sensed biological measures, the ACS can assist in higher level diagnostic assessment by, for example, asking the patient questions and assessing patient behavior and condition via a patient's responses. A post-event profile of the patient can be generated within an "event report" which can consist of information about the patient and the patient's environment that may be useful in assessing the degree and duration of trauma that the patient experienced, in relation to the occurrence of the event. The ACS can perform behavioral testing upon the patient and obtain behavioral responses that provide insight into medical status of mental, emotional, and cognitive state.

Behavioral responses can be used to quantify the seriousness a medical event and to provide diagnostic information to the medical practitioner both during and after the occurrence of a medical event. For example, behavioral testing can indicate if a patient lost consciousness and if so for how long. Further, answers to pertinent questions can assist in assessing symptom severity in manners that may be difficult or impossible to obtain by processing biological data (for example, using sensed cardiac data would not be very good in assessing the level of pain, numbness, or tingly-ness which a patient is experiencing). Due to the provision of audiovisual recording capacities, the ACS may store a multimedia log of activity related not only to an event, but to the patient's environment, including exchanges with the emergency medical personnel. The ACS can thereby provide event-records which may serve in assisting in subsequent medical and medical-legal assessment of what occurred during the event.

While communication between the ACS and the central station is a main intended advantage of the ACS, this may not always be possible due to global gaps in cellular coverage. The ACS provides a plurality of mechanisms and methods by which communication can be established when a primary mode of communication (e.g. cellular communication) is not available. Once communication is established, the ACS provides novel features by which the central station can process and respond to the alert signals sent by the ACS. The use of alert 'context-tags' allows efficient processing of the alert signals sent to the diagnostic station from the patient and enables medical practitioners at the diagnostic station to delay processing of incoming alert signals which have priority values indicating that they are non-urgent. In the case of urgent alert signals, the ACS features increase the likelihood that communication between the station and the patient is efficient and clear, for example, by providing communication via a translator and/or web-based interface.

DETAILED DESCRIPTION OF THE INVENTION

In the following description, the term "module" refers to electronics, software programs, communication, operations, algorithms, methods and strategies related to accomplishing the task of that module. Although modules are illustrated as isolated, the components of the modules can be distributed, and may operationally rely upon components of other modules.

Patient state information pertains to the physiological, emotional, mental, periodic (e.g., circadian), or environmental state of a patient. "Patient state information" includes, without limitation, physical state (e.g. walking, supine, sleeping etc.), time of day, patient input, evaluation of sensed data related to body temperature, blood pressure, or other available measures. "Patient state information" may also include heart related features such as heart rate, the presence of arrhythmias, as well as acoustic or chemical measures related to cardiac function, which may be obtained. Patient state values can include a patient's mental state (e.g. angry, confused, slow, unconscious), as may be derived based upon a patient's input in relation to a digitally implemented questionnaire, reaction time tests, or behavioral testing programs which are implemented by the system.

The Alarm and Communication System (ACS)

Figure 1A:
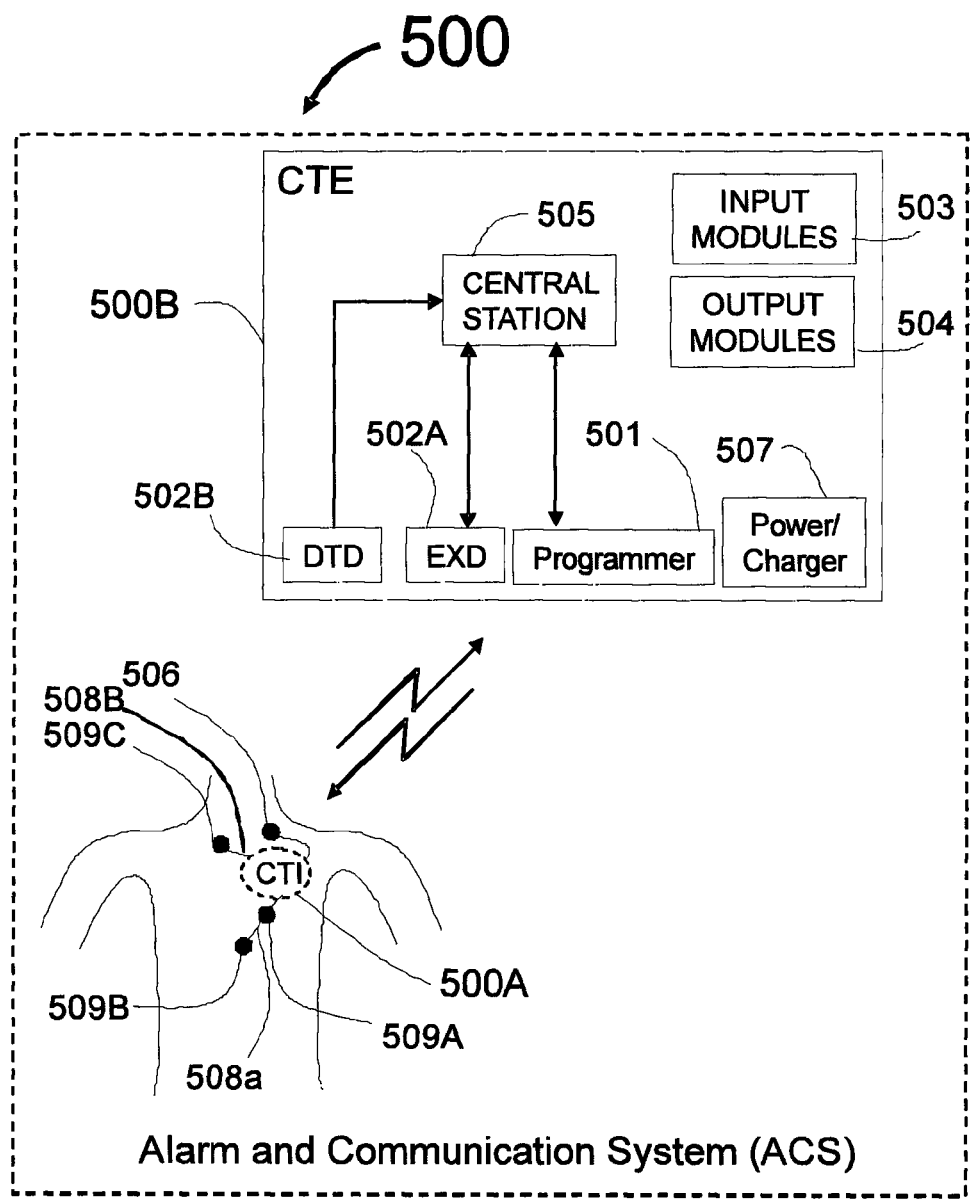
FIG. 1A illustrates a schematic representation of a preferred embodiment of the alarm and communication system comprising an implantable system and an external system.

FIG. 1A illustrates one embodiment of the ACS 500, which contains an implantable Cardiotrend system (CTI) 500A and an external cardiotrend system (CTE) 500B. Since the ACS can be realized as a Cardiotrend system, or as a system designed to assess neurological or other type of disorder, the CTI 500A should be understood to generally refer to implantable components of the ACS. Additionally, the CTE 500B may communicate with and/or control generic implanted detection and/or stimulation devices. The CTE 500B may include an external device (EXD) 502A, that is implemented as a pager type device worn by the patient. The EXD 502A. may also be secured to the patient's skin, for example, using an adhesive patch, and can have dermal, trans-dermal, or sub-dermal sensor components, such as electrically conductive pads for sensing the patient's biological activity. The CTE 500B would typically include patient alerting capabilities (e.g., vibratory, acoustic or visual) and could be designed to include wireless voice and data capabilities. The CTE 500B will typically communicate with the CTI 500A using bidirectional wireless radiofrequency transmission, and may be used to provide the CTI 500A with operator parameters in order to program the operation of the CTI 500A, as will be further described below. The CTE 500B has buttons by which the patient can mark events, navigate through and select menu items, and, control and monitor CTI 500a operations such as communication with a central diagnostic station 505. The CTE 500B can also communicate with subdermal and implanted sensors and stimulators that may operate and be powered relatively independently or which may be implemented as part of a sensing or stimulation network.

The (CTI) 500A may communicate with other implanted devices (not shown), a physician programmer 501, a portable patient external device (EXD) 502A, or a home patient data transmission device (DTD) 502B which may be a limited version of the physician programmer 501. The programmer 501, EXD 502A and DTD 502B may have an input module 503 that may include a keyboard, mice, various control buttons, audiovisual recorders and communication transceivers (e.g., telemetry circuitry) hardware. The programmer, EXD 502A and DTD 502B may have an output module 504 that may include various displays, alarm transducers, multimedia capacities, a (wireless) modem, and other communication equipment. The programmer 501, EXD 502A, and DTD 502B can communicate with a central station 505, which may provide primarily automated processing of incoming patient data and which may include a staff of medical practitioners who can assist the patient when the system 500 alerts the patient that medically significant activity has been detected.

Figure 1B:
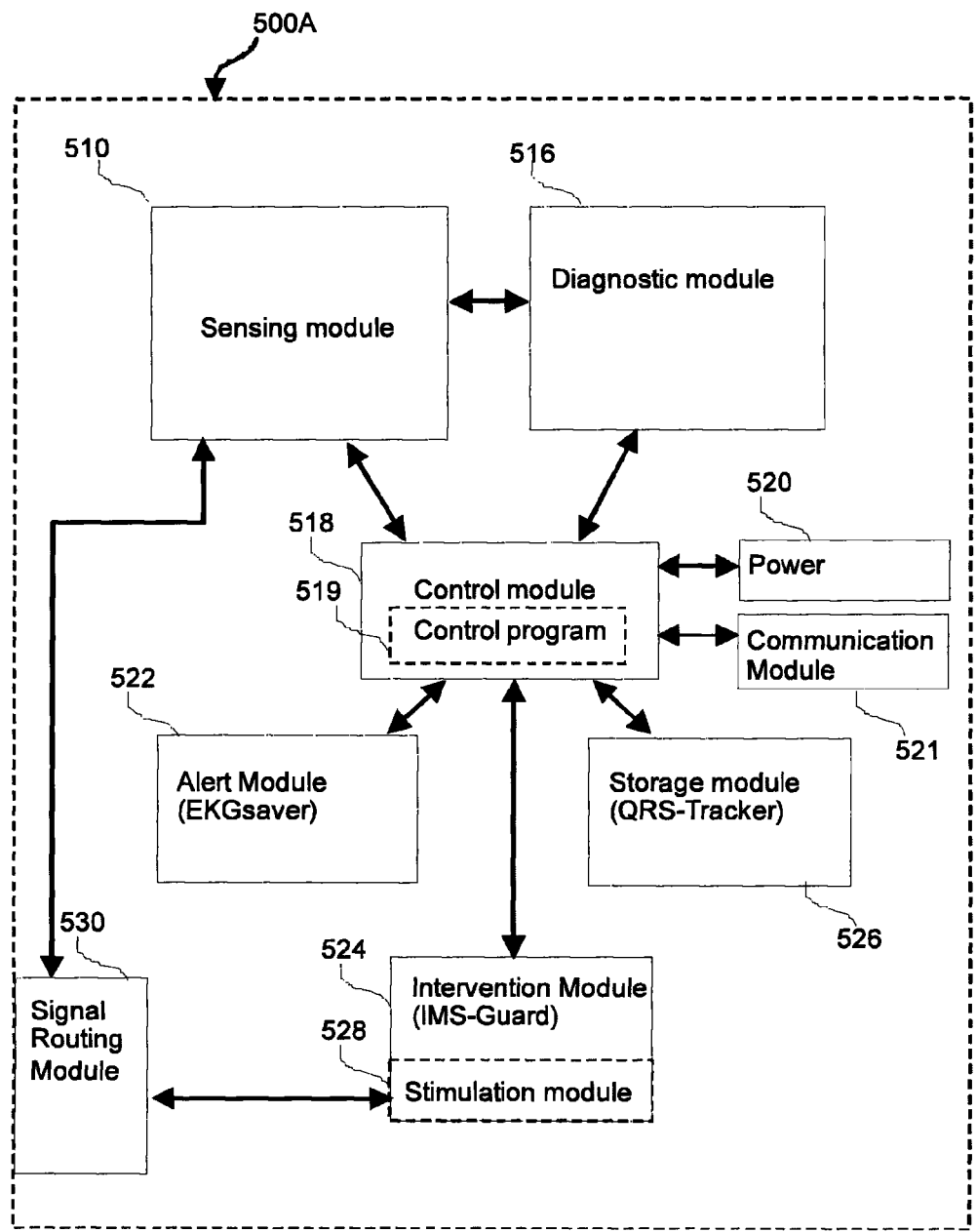
FIG. 1B illustrates a schematic representation of a preferred embodiment of the modules within an implanted portion of the alarm and communication system.

Power and charging equipment 507 can charge both the rechargeable power supply 520 of the CTI 500A shown in FIG. 1B and can recharge and/or supply power directly to CTE 500B components. The system can utilize sensors 506 and stimulation conduits 508A. When the sensor and stimulation conduit are both electrical, these can be realized in the same structure. For example, when a stimulation conduit 508A is a lead with contacts 509A, 509B, or 509C of a different lead 508B, then this can be connected to the stimulation module 528 shown in FIG. 1B via the signal routing module 530. When the contacts 509A, 509B and 509C are used to sense data, these can be connected to the sensing module 510 shown in FIG. 1B, via the signal routing module 530.

Other sensors, such as 506, may sense data related to optical, chemical, sonic, pressure, flow rates, and impedance characteristics of the patient. Signals from these sensors can be transmitted to the sensing module 510 through the signal routing module 530. The sensed data can come from sensors located external to the housing of an implanted device, or may be derived from components such as an accelerometer or thermometer which are located either within or outside of the housing, and which provide signals to the sensing module 510 as may occur using the signal routing module 530.

FIG. 1B illustrates, in block diagram form, an embodiment of the CTI 500A, which includes a sensing module 510, a storage module 526 with an associated random access memory, a diagnostic module 516, a control module 518, an alert module 522, a signal routing module 530 an intervention module 524, a stimulation module 528, a communication module 521, and a power supply 520. The control module 518, diagnostic module 516, storage module 526 will typically be implemented by a digital processor (or different digital processors) and associated software. The sensing module 510 controls the sensing of signals (including patient state related data) from the human patient and typically includes amplifiers, multiplexers, and other electronic circuitry related to communication with the sensors 506 and contacts 509A, 509B and 509C. The diagnostic module 516 is designed to analyze monitored data including sensed data provided by the sensing module 510, as well as data from the storage module 526 in order to produce "monitoring results" including detection of medically relevant events which are used by the control program 519 of the control module 518 to responsively provide alerting or other ACS operations. The control module 518 and the rest of the CTI 500A is powered by the power supply 520 which may be a rechargeable battery. The implanted system 500A communicates with other implanted devices and the external system (CTE) 500B using its communication module 521. The CTE 500B may be used to provide the CTI 500A with operator (function) parameters to customize the operations of the CTI 500A. These operator (function) parameters may be stored by the storage module 526.

As discussed, the operating components and functions described for the CTI 500A can generally also be implemented by the CTE 500B. The control module 518 of the implanted system 500A can be primarily controlled by, work in conjunction with, replaced by, and communicate with, the control modules residing in the external components 500B of the system. While the sensing module 510 of the CTI 500A can operate implanted sensors, the sensing module of the CTE 500B, can operate to sense data from external sensors.

The Control Module.

The control module 518 is designed to control the operation of the CTI 500A including the diagnostic module 516, the alert module 522, intervention module 524, and storage module 526 based upon the control program 519. Operation and control of the various modules of the ACS 500 are termed ACS operations (ACSOs), which are operations involving sensing, alarm, intervention, diagnostics, communication, storage, or other operation carried out by the alarm and communication system 500. ACSOs of the CTI 500A can be accomplished either by the control module 518 controlling the other modules of the CTI 500A directly or by the other modules acting independently under instructions from the control module 518. The operations accomplished by the control program 519 of the control module 518, can be triggered or modified in response to one or more "monitoring results" provided by a diagnostic module 516, or due to commands sent by the programmer 501, EXD 502A or DTD 502B of FIG. 1A. The ACSOs may also be triggered or modified in response to times which may be defined in the control program 519. When the invention is primarily oriented towards treatment of cardiac disorders, the alert 522, intervention 524, and storage 526 modules are specifically designed to monitor cardiac activity and exist in preferred embodiments known for the purposes of the present invention as the 'EKGsaver', 'IMS-Guard', and 'QRSTracker' (or 'QRS-Tracker'), respectively. The acronym IMS, stands for implanted medical system.

The Patient External Device (EXD).

Figure 2:
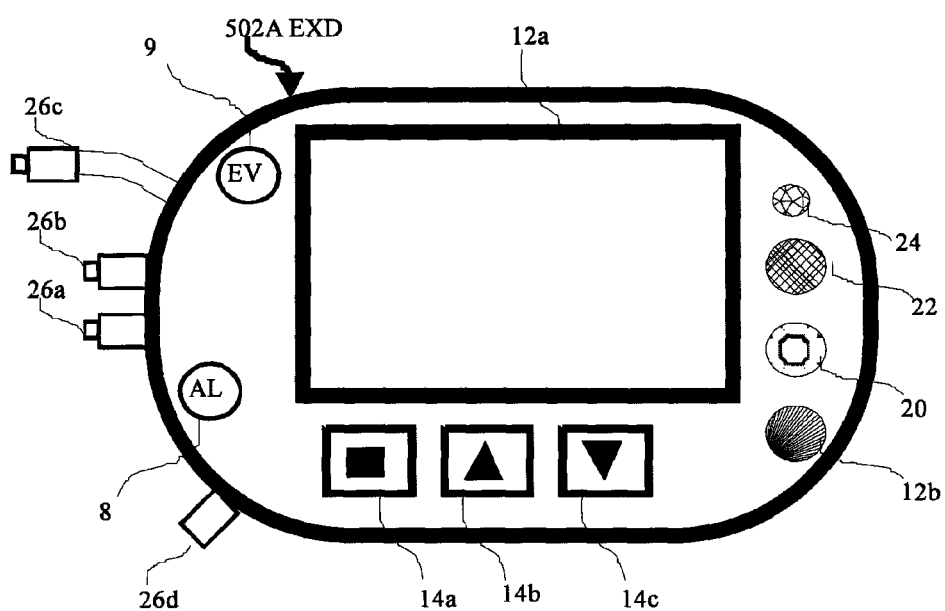
FIG. 2 illustrates an embodiment of a device external device (EXD) of the alarm and communication system as embodied within portable pager device, which is a preferred embodiment.

The EXD 502a can be realized as pager device having innovative input and output modules to implement novel features of the invention. As illustrated in FIG. 2, a plurality of communication connectors (26a, 26b, 26c) can establish communication with a central diagnostic station 505 using different methods. The communication connectors 26 can include port connectors such as a USB connector, a Firewire connector, a connector for a cell phone or PDA (e.g., Blackberry), a modem connector, and can also include connectors/transmitters which enable wireless communication connections to be established (e.g. infrared, cellular, BlueTooth). Future generations of communication connectors are implicitly included in this group of connectors, as are circuitry and protocols for establishing successful communication with various communication devices.

Communication connector 26d, is a communication component for providing communication between the EXD 502a and CTI 500B, and may occur via a wireless connection, sound, RF transmission, magnetic field, or by other manner, as is known to those skilled in the art. The EXD 502a can also include a visual alarm transducer 20, such as a bright multi-colored LED, which can emit different colored alert signal patterns to indicate the severity of a detected medical event, a speaker 22 for voice and sound presentation; a microphone 24 for recording voice messages, for allowing verbal commands (via speech recognition software), and for allowing verbal communication to occur between the patient and the central station 505. A visual output source 12a, such as a text and/or a video screen, allows visual alarms to occur as well as providing graphical menu items through which the user may navigate. The visual display 12a can also be used to present the user with behavioral testing questions, video message alert signals, interactive video communications with the central station 505 or physician.

The EXD 502a includes a visual input source 12b such as a digital camera or video recording device, which can comprise a wide-angle lens that is able to record across approximately 360 degrees. For example, the input source 12b may consist of a 3-camera system which records 3 video feeds from a triangular representation of the patient's environment. Compressed multi-media data obtained from the sound 24 and visual recorders 12b, can be stored and transmitted to the central station 505. Although the components of the EXD 502a are shown in FIG. 1 as extending from the device, the various connectors 26 can be rotatably or otherwise mounted within the housing of the EXD 502a and can have an 'operating' position and a 'storage' position.

The EXD 502a can also include a patient-initiated alert button 8 which the patient can press in order to indicate that he/she believes a harmful, dangerous, or disruptive medical event/condition is occurring. In order to prevent the alert button 8 from being un-intentionally pressed, there may be a false-alert preventative measure provided such as requiring that the button 8 be pressed according to a specific pattern (e.g., slowly for 3 successive presses). Alternatively, the false-alert preventative measure may be an actual physical barrier which prevents unintentional alarms. The false-alert preventative measure could also consist of a message to the patient that requires the patient to confirm that the button press was intentional. Patient-input buttons 14a, 14b and 14c, may be a designated "select", "up", and "down", respectively, or may have other designations which enable the user to navigate through, and select from, menu items and parameter values related to operation of the system 500. Patient input buttons 14 can be used by the patient to select menu items that describe a particular alert or event. Similar to the BlackBerry™ device, the EXD 502a can be configured with a keyboard or can have connection for a keyboard, which may be physical or enabled via Bluetooth.

The EXD 502a can also include at least one patient-initiated event button 9 that enables patients to mark the occurrence of events such as the beginning and end of activities. Patient-indicated events are different than patient-initiated alerts because these will usually not merit immediate medical attention or communication with the central-station 505. The patient-event button 9 (and the input buttons 14) can be used to define events such as indicating the beginning and end of an exercise period, or an episode such as dizziness, numbness, shortness of breath, or other unwanted symptom which is not a major medical event. The physician may ask the patient to mark events such as walking, running, swimming, sleeping, driving, or other activities for which normative data may be useful. The EXD 502a can store data related to these activities in order to record samples of their cardiac or physiological correlates and may store or transmit these at either the current or later time, such as when the patient has convenient access to a computer. The physician or medical personnel at the central station 505 can use this data in order to build a patient profile in a database, in order to better understand patient-specific variability. Further, cardiac phenomena such as ischemia can result from heightened activity such as exercise, and the central station 505 can analyze any transmitted data according to recent patient-initiated event marking as indicated by the event button 9 (e.g. the data will be interpreted differently if it was sent just after an exercise period rather than just after the patient has awoken). A historical record of recent events or alerts whether detected by the system 500A or patient-initiated using buttons 8 or 9 can be included with an event-tag that is sent with the incoming data. The manner by which the data are analyzed may be altered by the event tag information that accompanies the data transmitted from the EXD 502a.

The depressing of the event button may cause the EXD 502a (or CTI 500A) to store monitored activity so that this can be used as self-norm data, to permit subsequent offline examination in order to gain understanding as to different states or symptoms of a patient. Alternatively, the event button 9 may be used to signal the occurrence of an event which is defined as an event for which the EXD 502a should send data to the central-station, although this will normally be sent with an event-tag having a priority parameter value which is lower than that sent with patient initiated alerts. The lower priority value can indicate the data is merely sent for storage purposes or because a physician requested such a record be sent for offline review.

Rather than being configured as a pager type device, the EXD 502a can be realized within a USB memory stick (e.g. flash-drive) structure which is worn around the patient's neck or kept in their pocket. This can be about a third the size of the pager implementation shown in FIG. 2, with only a portion of the components. Alternatively, the EXD 502a can be implemented in a wrist-watch device having buttons for patient input, an LCD screen for displaying alert signal and messages, a speaker and microphone for audio communication, and other features shown in FIG. 2.

Figure 3:
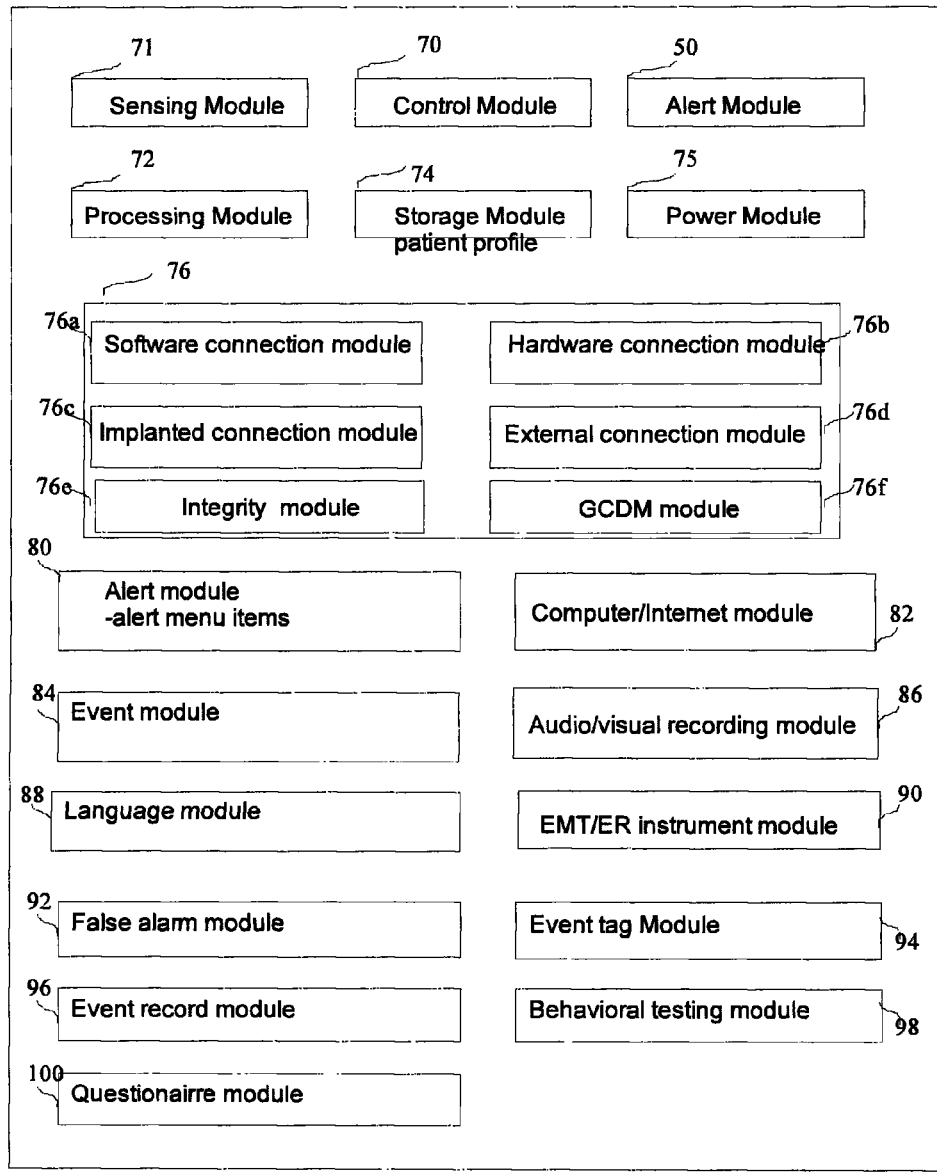
FIG. 3 illustrates a schematic representation of an embodiment of the EXD and its modules and subsystems.

FIG. 3, shows an embodiment of the EXD 502a including a control module 70 which controls the ACS according to a control program. As has been described in provisional U.S. 60/767,073 Systems and Strategies for Long-Term Monitoring of Cardiac Status, the control module 70 controls the operations of the other modules of the ACS, such as a sensing module 72, storage module 74, and alarm module 50. The sensing and storage modules are described in details in this other application and only the alert module 50 and various components utilized to provide alerts (76-100) are referred to and described in depth. The processing module 71 of the EXD 502a can detect events using data it senses form external sensors as well as data sent to it by the CIT 500A. It should be understood that the EXD and CTI can work together in order to detect medical events. The EXD can not only be implemented as a pager device that is capable of obtaining user input and accomplishing behavioral testing, but further, the EXD may include or communicate with sensors that may sense data from sensors located external to the patient (e.g. an EKG sensor array affixed to the patient's chest or a vest that the patient wears which contains biosensors). A medical event may be detected by the data obtained by the external sensors, the internal sensors of the CTI, or an analysis which utilizes both internal and external data in order to detect a medical event. Medical events can be detected using only internal data, only external data, a combination of the two, and further, if the external or internal data detect an event that is not present in the other data set, this itself may merit sending the data to the central station 505 for further review.

In addition to facilitating data analysis and communication between the patient the central station, the EXD 502a can allow the central station 505 to play a role in adjusting the therapy provided to the patient by the CTI 500b. For example, the EXD 502a can be provided with a control module 70, which can accept commands from the central station. Thus methods of intervention can be provided by the central station 505 in conjunction with the EXD 502a to influence the operation of the CTI 500b. In the first method, the medical practitioner of the central station can remotely modify a stimulation therapy program of the CTI 500b, so that stimulation occurs in response to an evaluation of cardiac activity by the practitioner. This type of remote intervention can also occur in a prescription-based manner if the primary care physician has previously prescribed a change in the stimulation parameters which should occur in response to certain types of cardiac activity profiles, and this change is noted in the patient's profile stored at the central station. The control module 70 of the EXD 502a can be programmed to allow or prohibit this type of action being allowed (some patients may not wish to allow remote adjustment of their implanted device). Two simple types of modifications involve increasing the stimulation signal or stimulating for a longer duration across a given interval. The EXD 502a can also contain a stimulation treatment parameter value in its control module 70, which causes the CTI 500b to modify a programmable valve structure that functions as part of an implanted drug delivery system. The valve can feed at least two catheters, so that any drug which is supplied under control of the CTI 500b can be routed to at least two locations. This treatment parameter value can also be modified remotely according to a signal sent from the central-station 505.

Turning now to FIG. 3, a schematic embodiment of the EXD 520a is shown. The EXD 520a includes a control module 70 which controls operation of the EXD 520a and other components of the ACS 500. An alert module 50 operates an alert/alarm program which can implement a number of alert/alarm protocols. Each of the alert/alarm protocols contains alert/alarm parameters, and changing these parameter values causes the protocols to be implemented differently by the alert program. For example, an alert/alarm protocol which implements a waiting duration before performing an operation, will utilize different durations based upon the value of the relevant alert/alarm parameter. The different protocols and parameters can be stored in the storage module 74, along with other stored information including patient data, norms, patient preferences, and patient profile information. The storage module 74 can be a queriable memory structure which also stores raw data features, trend data, and statistics related to the data which can be monitored as part of the ACS 500 operation. The ACS 500 can be realized as a device which only provides patient alerts, storage, and communication with the central station when the patient initiates an alert or event by pressing the button 8 or the button 9. However, in most embodiments, the ACS will monitor some type of data, and this data can trigger alerts when the processing module 71 detects some feature in the sensed data which has been defined to be abnormal or is a medically relevant event that has been otherwise defined as sufficiently important to merit the triggering of an alert. The sensed data is obtained from the sensing module 72 which communicates with sensors or which obtains sensed data from the implanted device 500a, using its communication module 76.

The communication module 76 allows for communication with implanted devices and external instrumentation, using modules 76c, and 76d, respectively. The communication module 76 allows communication between the EXD 502A and the central station 505 using different communication protocols and methods. The communication module 76 contains protocols, programs and methods for permitting, for example, wireless communication as well as allowing for data transmission to occur using land phones. Communication can also occur using the internet and any generic computer attached thereto, and is facilitated by providing for automatic driver interface and installation routines. The communication module 76 contains a software connection module 76a which includes lists of connection phone numbers which can be used to establish both wireless and physical connections. The list can contain (toll free) access numbers and access codes for establishing communication in different geographical locations. According to one aspect of the present invention, the communication module 76 may be configured to obtain a patient's location using a GPS or other positioning system (e.g. cellular or WiFi triangulation methods), and then operate the communication module 76 to automatically select access information to efficiently establish communication between the patient and a central station 505 while the patient is traveling worldwide.

The software connection module 76a permits communication between the EXD 502A and other devices, and includes 1-800 numbers, local access number, area codes, country codes, and city codes for allowing the ACS to effortlessly connect wirelessly, over an internet connection, or over a phone connection without the issue of long-distance access becoming an issue. When the 1-800 is for an ISP then internet access may be provided. The software connection module 76a also contains the connection routines, identification codes, and security encryption programs. The software connection module 76a also includes logon and password access information to access internet service providers and establish wifi, wireless, and land based internet connections. The software connection module 76a also includes connection routines and protocols for establishing the identity of the EXD 502a and the patient during initiation of communication and handshaking routines, as will be known to those skilled in the art. The connection hardware module 76b contains the circuitry and hardware needed to operate the different connectors 26 of the EXD 502a, including cell phone connections, firewire connections, USB, Ethernet, modem, smart-card, wireless, GPS receivers, antennae for radiofrequency transmissions, and BlueTooth. The communication module 76 also contains an integrity module 76e which ensures that communication between devices occurs as expected. For example, the module 76e should be able to determine how long it might take to send a certain amount of data and can provide an error warning if data transmission is taking longer than expected. Lastly, the generic communication device manager (GCDM) module is a specialized module that allows the EXD 502a to communicate with generic devices which may be external to the patient (EMT devices) or implanted within the patient (generic implantable devices).

The integrity module 76e can also serve to ensure that the ACS will function as intended. For example, the EXD 502a may not receive an alert signal from an internal device because no medical events have been detected in the data, alternatively the EXD 502a may not receive an alert signal because there is a problem with the communication between the two devices. Accordingly the EXD 502a can be set to periodically (e.g. once per day) test and confirm the integrity of communication between the two devices. The EXD integrity module 76e, can also have routines to periodically (e.g. every 3 hours) ensure that communication with a desktop system or central station is possible and can subsequently check data connection using integrity checks such as time-outs or "pings". This latter type of check may be set only to occur if the GPS software in the connection software module 76 uses the GPS system of the connection hardware module 76b to determine that the patient has moved into an area of low wireless coverage. The integrity module can also check the remaining battery life remaining of the EXD 502a and can send an alarm when this is below a specified amount (e.g., <2 hours).

The alert module 50 contains rules, protocols, parameter values, and alert-related subroutines that are used to provide the alert signals in response to medical events. Primary (default), alternative, and as well as the local intervention alarm protocol (LIAP) protocols are defined as well as the rules for selecting these protocols. The alert module 50 permits different alert signals by operating programs that send alert signals using various modalities and multi-media methods including sound, visual, pre-recorded video, vibratory, and wireless signals. Wait parameters are defined which cause various time restrictions to be imposed prior to performing different steps of the alerting, such as waiting for a user response or attempting certain type of communication method. The alert module also allows the patient to customize alert signals and routines, and to adjust the protocols using menu items.

When the conditions for 2 alerts occur simultaneously, the EXD must be able to prioritize, ignore, or address at least one of these. The selection of alarm protocols occurs according to the alarm program and its parameters and settings and various strategies can be used to deal with this situation. However in one embodiment, each alert signal has a ranking, related to its importance, and protocols with higher rankings take precedence over protocols with lower rankings. For example, if an alert signal related to detection of exercise-related ischemic increase had a rank of 2 and an alert related to a major cardiac event had a rank of 1, then alarms related to exercise would be ignored in favor of the major medical event.

The alert settings may be adjusted to implement a number of alerts according to a number of alert protocol parameters which have been defined for both serious or minor detected events. The alert operations can be constructed in order to save energy of the CTI 500a and EXD 502a, and resources of the central-station 505 personnel, and in order to provide alerts which are appropriate to different patient's disorders. For example, four different alert protocols could be the following:

Alert 1: alarm patient+alarm central station+send data immediately
Alert 2: alarm patient+alarm central station+send data upon request
Alert 3: alarm central station+send data upon request
Alert 4: alarm patient+(alarm central station+send data immediately if patient accepts suggestion to send data)

These different alert strategies can be selected automatically based upon a detection of an event, based upon user preference, or can be adjusted based upon a patient's manual input (including in response to questions provided by ACS), or lack of input, for example, where the patient may be unconscious.

The computer internet module 82 contains programs for automatic driver installation and can contain programs and routines for connecting through the internet using a standard browser which automatically connects to an address of a remote server, or can contain its own specialized web-browser and data transfer programs. In one embodiment this module can be configured with AmericaOnline access numbers.

The event module 84 allows for different events to be assigned to different buttons of the EXD and controls what occurs when these events are triggered. The event module can also contain programs for recording voice descriptions when events occur.

The audio/visual module 86 allows for the analog-to-digital conversion of multi-media information as well as its compression and storage, allows for presentation of sounds and visual stimuli including video-based messages, allows for transmission of the multimedia information to the central station 505. The information which is stored in the storage module 74 of the EXD 502e can be different than the information which is sent to the base station 505 in that the module 86 can degrade the information which is sent or which is stored in the device in order to increase capabilities and decrease either the storage or transmission loads, respectively.

The language module 88 of the EXD 502e can provide for information to be presented to the patient in a default language (e.g., English, German, or Spanish) or alternative languages, and contains information about languages which the patient speaks or understands (this information can also be provided at the central station in the patient profile).

The EMT/ER module 90 can automatically identify, or permit an emergency medical technician or member of the emergency room staff to specify, the external equipment with which the EXD 502e will communicate and also has communication protocols for subsequently achieving this communication so that historical records of patient data may be uploaded onto other equipment. The EMT/ER instrument module provides programs and protocols for communicating with these external devices, for example, when the ACS is plugged into one of these.

The false alarm module 92 provides programs for deterring spurious alerts. For example, when an alert is triggered by the patient, the module 92 can as the patient, "are you sure?" so that false alarms are not automatically and inadvertently sent to the central station. The module 92, can also define alerts or events as only occurring when buttons of the Exd 502a are pressed in a particular pattern, and within a particular interval.

The event-tag module 94 allows the EXD 502a to submit tags which contextualize the data being sent to the central station. For example, voice tags can include verbal descriptions of the data. Priority tags can indicate if the priority of an event and whether the data should be reviewed immediately due to medical urgency. The event tag module may present a beep after an alert signal is issued and then give the patient a period (e.g. 10 seconds) during which a verbal description can be automatically supplied.

An event-record module 96 contains routines for recording post-alert data concerning patient behavior and their environment. The module 96 can contain routines for automatically initiating a multi-media recording which lasts until the patient authorizes its termination or memory is exhausted. The event-record can serve to provide evidence of what occurred after the medical event occurred. This record can be useful in enabling a physician to evaluate what happened to a patient. This type of record can also be beneficial in medical-legal issues since it can provide a record of what assistance the EMTs provided to the patient. The event record module 96 can use the audio and video 12b, 22 recording devices of the EXD 502a.

The behavioral testing 98 module provides behavioral tests, obtains patient responses, and evaluates these responses in order to provide a behavioral record of the patient's condition. This may be especially important in cases of stroke where testing can determine how badly the patient has been affected as well as the time course of any deficits or deterioration. In addition to reaction times and accuracy, the test scores can be scored in manners specified for the particular tests administered.

The questionnaire module 100 provides questionnaires either in the form of text messages or using a verbal or multi-media format. The answers can be provided using input buttons 14, or voice recording which can also contain simple speech recognition for answers such as "yes", "no", "unsure", and numbers 0-10. The questionnaires can be supplied in a predetermined format or can be dynamically adjusted based upon the user's responses. The duration for response, can be measured in responses to questions here as well.

Behavioral Testing

A post-event profile of the patient can be generated within an "event report," which can consist of information about the patient and the patient's environment that may be useful in assessing the degree and duration of trauma that the patient experienced, in relation to the occurrence of the event. One type of event report includes post-event behavioral testing of the patient. The EXD 502*a* can provide several types of behavioral testing. One type of testing involves is sensory-motor processing, including reaction time tests (e.g., press the button quickly after an LED is flashed), manual pursuit tasks (via a mouse/navigation button) where the patient must keep a moving dot within a circle that they control. Behavioral testing of cognitive tasks can include a simple Stroop task where responses can be verbal and be recorded or can be button presses, geometric tasks (e.g., choose a particular shape from several shown, which is larger, which has more corners?) Questionnaires can also provide insight into cognitive processes both with respect to accuracy and reaction times. Questions such as "what day is it" can be presented with a display of the days of the week, from which the user must make a choice.

If a digital keypad is displayed, patients can be asked to supply dates such as the current year, year of birth, and age. A digital keyboard would also allow tasks such as mathematical questions (e.g., 2*18) or tasks (e.g. start at 101 and subtract 7) to be provided, although these can also be verbally presented using "WMV" files. Questions can be specific to symptoms of a disorder which the patient may be experiencing, for example, "are you numb?", "are you in pain?" The answers can be compared to a patient's previous answers (e.g. self-norm data) and a score can be generated based upon a comparison of the current responses to previously supplied answers in order to generate scores for reaction time and accuracy. A patient's response may be obtained by button presses or verbal responses. The testing may be done in conjunction with or under the guidance of the medical practitioner at the central station. The response may be stored in memory, and verbal responses can be submitted to voice recognition, especially for simple responses such as yes and no. In order to make the task slightly more interesting user designed questions may also be provided which the patient has previously entered "Who was MVP of Superbowl 40", "Who won the World Series in 1961", where the patient can scroll through a list of choices to select the correct response.

Figure 7:
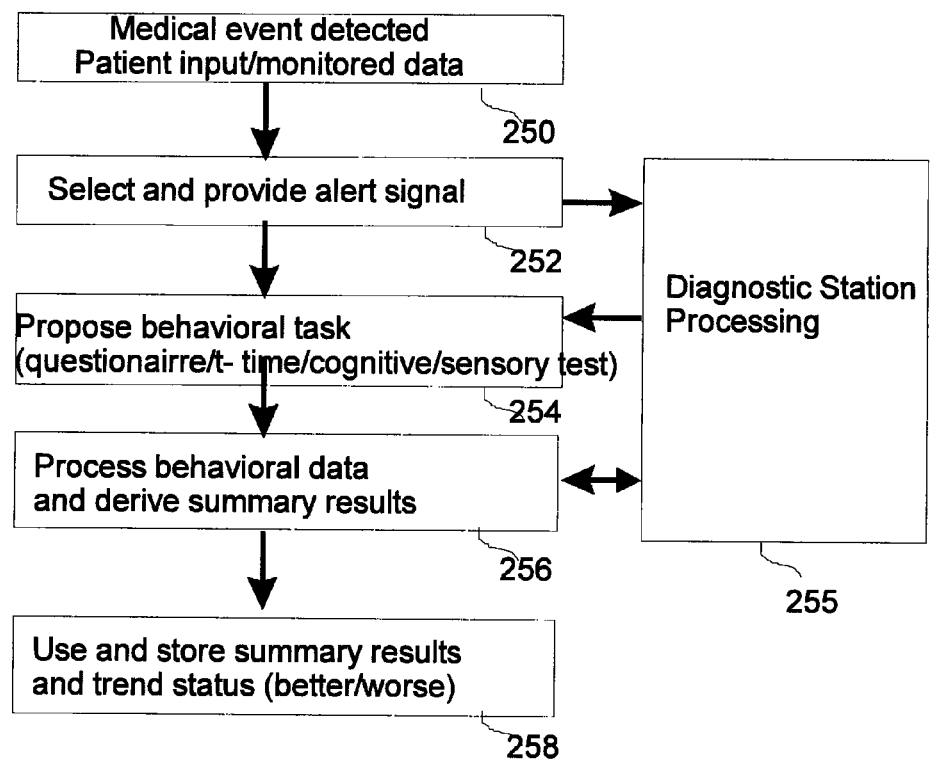
FIG. 7 illustrates a method by which the EXD provides behavioral testing in order to provide a behavioral record or to evaluate the patient's condition.

FIG. 7 illustrates a method by which the EXD 502A provides behavioral testing in order to provide a behavioral record or to evaluate the patient's condition. In block 250, a medical event is detected based upon patient input and/or monitored data, as previously described. In block 252, an appropriate alert is generated and issued to the patient and also passed to a diagnostic station, as indicated by the error from block 252 to block 255. The diagnostic station 255 represents software/hardware in the EXD 502A and a possibly medical practitioner at the central station. In block 254, the patient is requested to perform an appropriate behavioral task. In block 256, the behavioral data is processed and summary results are derived. In block 258, the summary results and trend states (i.e. is the patient better or worse) are used to diagnose the patient and/or are stored.

Event Tags

If the medical practitioners at the central station are forced to monitor and evaluate all incoming data, even when this data is being sent by patients for reference rather than alarm reasons, this will greatly increase their workload. Alternatively, certain events may cause the EXD 502*a* to send alert data to the primary care physician for later analysis. The event button can cause an event menu to be displayed whereby the patient can select a menu item that describes the type of event which is has occurred. Further, the pressing of the event button 8 may cause other alternative non-critical tasks to occur which do not necessarily involve the central-station. For example, the patient event button press can cause medication to be dispensed from a medicine module, which may be in the housing of the device 10.

The initiation of an event or alert can result in a 5-10 second window where the microphone is automatically activated and the patient can make a verbal note as to what is occurring (e.g., what caused the pressing of the respective button). This verbal note can be sent along with the data from the EXD 502*a* to the central-station 505, in order to contextualize the data. The verbal note can undergo speech to text conversion prior to being sent or at the central station itself. The event tag can serve as a context tag which includes a priority value indicating if the incoming data is urgent or non urgent. The context tag can also include an event value indicating the data relate to an event type (e.g. exercising) for which the incoming data is relevant. The context tag can include a verbal description of the context for the data. Context tags can be included in the header of the data file and can include patient preferences such as a language preference for the patient, and a language ability level of the patient, although this should also be included in the patient profile stored at the central station 505 (it may not be known to EMT personnel who interact with the EXD 502*a*).

In systems where a "panic" button is provided and triggered by a button press, or by other means, data is often simply automatically sent to a central-station and the medical practitioner ostensibly must respond by contacting the patient to evaluate the situation. The methods described here provide a number of advantages with respect to what may occur in response to the pressing of different buttons, and requires less back-and-forth communication between the central station and the patient. By tagging data sent to the central-station with a verbal message or by other means, the efforts of the central-station personnel are not wasted, and time and energy is also not wasted for the patient who has to respond to the attempt at communication made by the central station's medical practitioner. By enabling incoming data to be tagged with a priority or other score which indicates if review of the data is necessary, the workload of the central station will be reduced dramatically, especially if several hundred records are transmitted each day.

Local Intervention Alert Protocol (LIAP)

While sending alerts and data to the central station 505 offers a main advantage of the ACS 500, simply alerting the patient to the occurrence of an adverse medical event can also be lifesaving. Although heart-attacks can be both painful and fatal, they can also occur in ambiguous fashions and may even be undetected by the patient. A simple intervention or change in activity, such as stopping exercising, may deter or stop a severe medical event from evolving. Further, in certain disorders such as syncope, providing an alert can serve to notify bystanders that a serious medical event has occurred (e.g., the patient is not merely napping on the beach or a park bench, but rather suffering from a heart attack). Accordingly, in another alternative alarm protocol, termed "local intervention alarm protocol (LIAP)" the ACS communicates to people who may be in the vicinity of the patient using audio and visual alarms, including a warning signal such as a siren sound, loud beeping, and/or a verbal message such as "Emergency medical event, please press the red button 3 times for more information". According to one example of the LIAP protocol, the alarm program can cause this message to be repeated a number of times according to a specified schedule. When the red button (e.g. 9) is pressed correctly, a series of pre-recorded audio, audio-visual, or text messages can appear which can guide the good-Samaritan in providing assistance in various manners such as calling the central station, or calling an ambulance via 911, and giving them a specific message about the patient. The LIAP messages can include instructions for what to do until the emergency team arrives, and can include text/or auditory dynamic questionnaires which occur, or trigger new audio-visual messages to occur, according to the answers provided in order to provide appropriate care to the patient. The LIAP messages can also be timed, and can request certain information after every N-minutes. The LIAP protocol may be very important for seizure disorders, heart-attack, stroke, or syncope, or any other disorder where the patient becomes unconscious, or enters any other state, where the patient may not be able to appropriately address the situation without assistance. Simply alerting bystanders that a medical condition exists can be sufficient to save the life of a patient by getting medical treatment to the patient within a sufficient amount of time.

Primary and Alternative Communication Protocols.

A portable alarm system which facilitates tracking of and communication with a patient, utilizes GPS for tracking and satellite/cellular communication with a central station 505. A number of methods are provided for addressing what occurs when this communication either fails or is simply not available. Wireless communication may not always be reliable or available. While global coverage for both satellite and cellular devices is growing, there are still many regions of the world where these services are not provided. Further, in many buildings, elevators, etc, this type of communication is simply not possible. Even when a default alert mode utilizes a cellular system, the user may prefer to switch to a physical connection that establishes a connection over the internet, in order to transfer large amounts of data, or otherwise communicate with the central station. Non-wireless modes may also be preferable for non-critical communication in order to greatly reduce the cost of system use (e.g., while traveling abroad) and can therefore be preferably set as the primary mode, at least for selected low priority alert-related events.

In one communication method, the primary communication protocol is attempted until a communication criterion is not met, which can be defined by a "defeat" parameter of the communication protocol. For example, after a certain number of failed attempts at establishing or successfully transmitting data over a wireless communication the alternative protocols may be selected. The defeat parameter and alternative parameters can be adjusted based upon the patient's geographical location and proximity to known "successful" communication points. For example, an algorithm of the EXD 502a can calculate distance to closest cellular transmission point to enable patient to determine if they can easily get there in order to transmit data.

Figure 6:
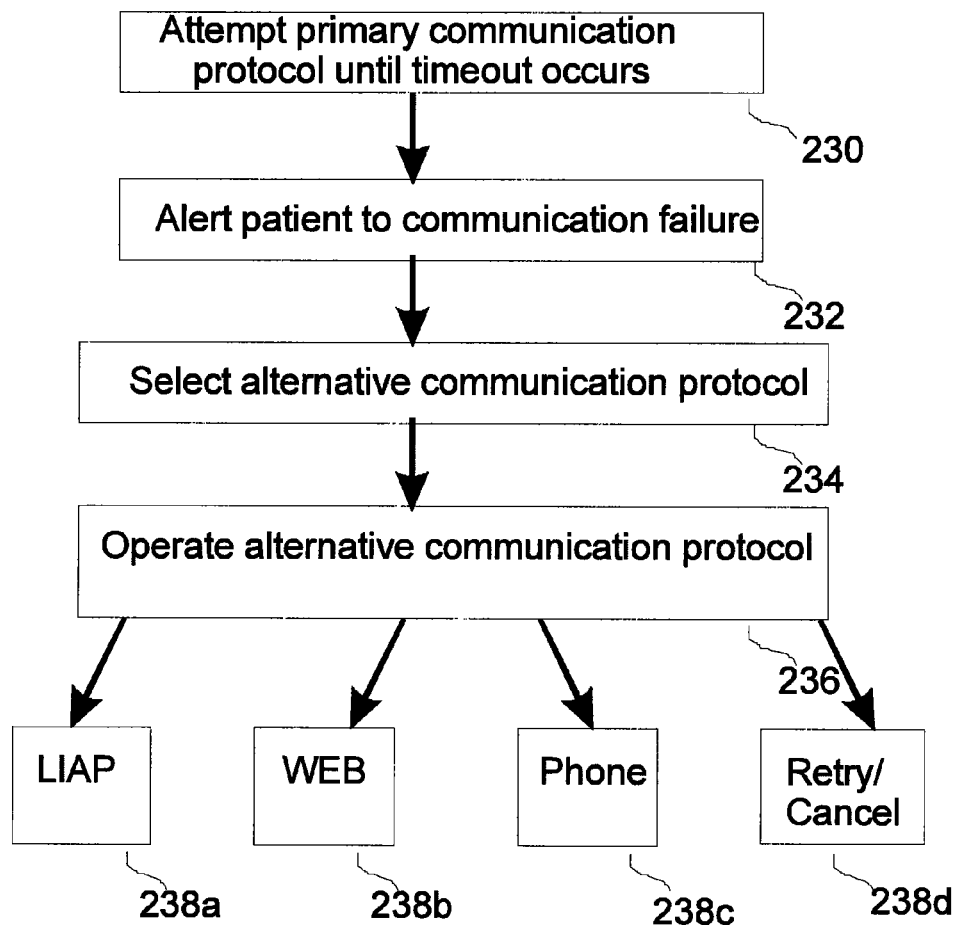
FIG. 6 illustrates an alert method which comprises utilization of a primary and alternative alert protocol which have different methods of establishing communication between the EXD and the central station.

Because satellite/cellular communication is probably the easiest method of communication between the ACS and a central station, this may often be set as the default protocol. The default protocol of the alarm/alert program should therefore have a "wait parameter", which specifies a duration during which the default protocol should be attempted prior to switching to an alternative protocol. FIG. 6 illustrates an alert method that involves this type of duration limited alerting. Block 230 shows that the primary communication protocol is attempted until a timeout occurs (e.g. after 2 minutes of attempts). In block 232, the patient is alerted to the communication failure, which may enable the patient to either select an alternative communication protocol, as indicated in block 234, or take some action that may enable the primary or alternative communication protocol to succeed (e.g. move to a location where the wireless reception is superior). Assuming that the primary communication will not succeed, in block 234, an alternative communication protocol is selected, which may be selected by the user, as mentioned, or may be selected automatically.

In block 236, the alternative communication protocol is invoked. As shown, the alternative protocol may include LIAP 238a, be web based 238b, or involve the telephone 238c. Block 238d also shows the possibility that the attempted communication may be canceled or retried.

The alternative alarm protocol can then occur under the guidance of a user or can occur automatically. Any of the alternative alarm protocols that will be described herein can be set as the default alarm protocol, according to user or other preference.

The EXD 502a should be able to connect to generic computers to send data via a high-speed internet connection or can even establish a connection if such a service is not available on the computer using a modem and 1-800 number. An alert protocol is provided where the EXD 502a communicates with a central station through a computer. The link between the EXD 502a and the computer can occur using a physical connection, such as a USB connection, or can occur using a wireless network of a computer. The computer can, in turn be connected to the internet, or can use a modem to transfer data over a phone line directly to the central station. Alternatively, the EXD 502a can have its own modem to establish communication with the central station over a phone line, either directly or, again, via the internet. For example, the EXD 502a may use its modem to dial a local access number such as an AmericaOnline™ access number, and can then utilize a customized routine which provides a username and password, in order to log into the internet, connect to a specialized server or website, and then transmit over this connection. 1-800 numbers for at least one ISP provider can be stored in the EXD 502a memory and iteratively attempted until successful communication is established. The accounts for these ISP providers are paid for by the service providing the central station in order to insure that these are active and available. This method offers a less expensive, more reliable, and otherwise improved manner of transmitting data from the ACS to the central station, compared to prior art methods.

In another embodiment, an alternative alarm protocol is provided in which the EXD 502a communicates with a central station through a cellular connection which is different than that which may be provided within the EXD 502a. For example, the connection can be provided by a cellular phone or PDA with cellular connectivity through which the EXD 502a can communicate. Different cellular devices have different ranges of coverage due to factors such as the different cellular networks to which these devices may communicate. It is preferable to supply the EXD 502a with at least one communication adapter which is capable of making a physical connection with a number of communication devices. Cellular devices currently offer ports for allowing external connections, for example, which allow connection to a computer's modem, and it is likely that in the near future, these devices will also have either, IEEE394, USB, or similar ports for enabling easy connection between the devices. When the EXD 502a communicates with the central station using a land-line or another person's cell phone connection, the EXD 502a can utilize 1 or more 1-800 numbers, in an iterative manner, through which it attempts establish a connection. The EXD 502a has a connection program in which, once connected, the ACS performs standard handshaking and security protocols before transmitting and receiving medical information related to the alarm.

In some instances, the EXD 502a may need to communicate with the central station using an internet connection, which may be mediated through a computer, phone (e.g., public phone with a LAN connection), or other device which does not belong to the patient. When connecting through a computer a problem arises because the computer must be able to recognize and communicate with the ACS. When connecting a peripheral device to the computer, the correct driver must usually be found and loaded before the device can 'talk to' the computer. Two alternative methods to manually loading a drive have been developed by Hewlett Packard and Microsoft, respectively, which will be termed "automatic remote driver installation" and "automatic local driver installation". US application 20020129353, entitled "Peripheral driver installation method and system" (the '353 application) describes a method of rapidly installing a new device. The general method is described as locating and installing a new peripheral driver on an operating system by plugging the peripheral device into a USB port, or providing it to a wireless network, wherein the device directly the computer to load the driver from a server located remotely on the internet. The device causes the computer to send information about the driver which is to be installed, and the operating system on which it is to be installed, to a central server which sends back the correct driver for rapid, automatic, and precise installation. Alternatively, US 20050278461 entitled "Self-installing computer peripherals" (the '461 application) describes a method of rapidly installing a new device wherein installing a new peripheral driver on an operating system generally comprises plugging the peripheral device into a USB port, or providing it to a wireless network, wherein the device automatically runs an internal routine which causes the computer to download the driver to be installed according to its operating system, from the device itself, and thereby also provides for rapid, automatic, and precise installation. These two methods allow peripheral devices to actually achieve the "plug and play" functionality, expressed by that concept. Accordingly, the EXD 502*a* can utilize either of these automatic driver identification and installation methods to successfully connect to any computer on an as-needed basis. Additionally the patient may user a computer to log onto a central station 505 website and can answer questions about the current operating system and then download a program that will install drivers and web-based communication programs.

Once the ACS establishes communication with the computer, via a USB or other manner, it can use several methods in order to establish communication with a central station. In one embodiment it can launch the default web-browser (e.g., Internet Explorer or Netscape Navigator) and cause it to establish a secure connection to a web-server, termed the 'central station web server', for communicating with the central station. Alternatively, the ACS can contain a software module which is a customized web-browser or information transfer program which will allow communication between the ACS and the central station. Since the ACS has both audio and video capability, it can allow for communication to occur between the medical personnel and the patient, even if the computer does not have a microphone.

Collaboration with Emergency Medical Team (EMT) and Devices

The ACS can provide an alarm protocol parameter in which after an alarm occurs, if this parameter is set to true, the EACS continuously, or at least regularly, stores data received from the IACS and from the surrounding environment. The EACS may contain a hard drive or flash memory of about 10 g-bytes or more. This is sufficient to record raw data, summary data, and trend graphs that are generated based upon the IACS data as well as voice and video data obtained from the microphone 24 and video camera 20 of the ACS. Audiovisual records can be stored in, for example, in MPEG format (the central station may also have electronic means to accomplish this storage). The record data can be downloaded by the emergency room when the patient arrives, and can be utilized at a later time, for example, for medico-legal purposes because it can provide a visual and auditory record of what has occurred for the patient. Multimedia data records can also be important when the patient becomes unconscious, or in order to assess the severity and duration of certain events which may not be evident from the recorded activity (e.g., how long did the patient remain in a certain state after an event occurred). Further, after an alarm is triggered, the use of multimedia recording can allow for a patient to perform a series of tests in response to stored audiovisual messages that request information. Multimedia recording also permits the use of this information by the medical personnel at the central station. For example, an automated test procedure may request that a patient count backward from 100 by steps of 3, may perform an interview and record the patient's responses, may ask the patient to press the buttons of the EXD 502*a* as may occur during a neuropsychological or other behavioral tests. These tests can evaluate the severity of the post-stroke, post-syncope, or post-cardiac-event dysfunction.

The ACS can also be provided with a connector 26, such as a USB connector which can be plugged into various EMT- or ER-related instruments. The EXD 502*a* has an EMT-ER-communication module 90 which can identify and communicate with a number of models of generic or specialized instrumentation. Such instrumentation can include a specialized analysis/transmitter/storage system which obtains data from the ACS and sends it to the ER or primary care physician in a customized format. Alternatively, the instrumentation can include, generic and external auto-defibrillators (e.g., Life Pac™), basic life support systems, drug-dispensing instruments, EKG or EEG analyzers, displays, or recorders which are used by the EMT and ER staff, and with which they are well acquainted. The data from the CTI 500*b* can be downloaded, recoded, displayed, utilized, and evaluated by these EMT components.

It is a main advantage of the EXD 502*a* that it can communicate with sensors, such as an externally worn pulse oximeter, EEG or EKG monitor (e.g., holt-monitor device) using its communication subsystem 76*e*. It may utilize data collected from externally located sensors rather than, or in addition to, communicating with implanted sensing devices or the CTI 500*a*. The EXD 502*a* can offer a general alarm capacity which it achieves by monitoring data from these sensors, and can store this data, and also provide an alarm signal when a measure from one or more sensors indicates an event for which an alarm is defined to be triggered.

It is a main advantage of the EXD 502*a* to provide a feature where a local warning message is displayed so that people in the vicinity of the patient are alerted to the patient's condition, and do not simply think the patient is sleeping, homeless, or demented (e.g., if the patient is in a confused or fugue state, or has collapsed on the street).

Collaboration with Generic Devices Using the GCDM.

Advanced warning system features may be incorporated into a pacemaker or defibrillator. If certain features are incorporated into a specific pacemaker or defibrillator, then patients will be limited to choosing a pacemaker manufactured by the company that provides the AWS. This may not be the best pacemaker (or other implanted device) which is commercially available, or may not contain specific features available in a particular pacemaker which is particularly oriented towards a patient's particular disorder. Alternatively, the IPG may have been implanted at a previous time, and the incorporation of the AWS which is incorporated into a new IPG, would require a subsequent operation which entailed removal of the old IPG and implantation of the new one. Instead, incorporation of the AWS into therapy can be provided by linking the AWS functions with those of generic pacemakers or ICDs, and providing communication circuitry and programs in an device communication module, which enable collaboration between the AWS and different generic devices to occur. This specialized communication module for communicating with implanted devices, including its programs, algorithms, methods of communication, identification, and control, as well as its related various circuitry, is subsumed under term "generic communication device module" or (GCDM). The module can include both programs as well as physical interface which may be a communication port which can be physically connected to an implanted generic stimulation device or its external patient controller and which is configured to communicate therewith. Alternatively, such communication can occur via telemetry.

It is an object of the current invention to provide an ACS device which will communicate with generic pacemakers, stimulators, neurostimulators, defibrillators, and drug pumps, either directly, or via their external patient controllers. Accordingly, the ACS is provided with a GCDM, within its communication module. The GCDM can be implemented with different programs related to commercially available IPGs. For example, if the VITALITY 2 DR program was loaded into the GCDM then this would allow the ACS to communicate with the Guidant VITALITY IPG, while if the ZOOM® LATITUDE™ program was loaded, this could allow communication between the ACS and an LATITUDE's external programmer, which could, in turn, communicate/control this type of IPG. The GCDM could use its own analysis protocols and sensing equipment to evaluate cardiac activity and can then send control signals to the generic IPG, and/or produces an alarm signal, when evaluation of its sensed data indicated this was appropriate. The GCDM has not been explicitly described or implicitly suggested in the prior art and would allow the ACS to work with virtually any commercially available implantable device that has sensing or sensing/stimulating capability, without being formed within that device.

In another embodiment of the ACS the ACS serves as a treatment evaluation device. For example, if a generic IPG stimulates the heart normally in order to deter events. The ACS can obtain a signal from the IPG when it is stimulating responsively, or, alternatively, a sensor of the ACS can detect the stimulation signal of the IPG automatically, and not require a trigger signal to be sent from the IPG to the ACS. The data before and after (or simply after if the data is not continuously collected in, for example, a circular buffer) the trigger pulse can be analyzed by the ACS in order to determine if the therapy was effective, and an alarm can be sent if therapy is not effective for a specified number of attempts or for a specified amount of time. This can allow for customized analysis to be accomplished using various FDA approved devices which are implanted, without having to obtain FDA approval of the customized routines. The ACS would not affect the closed-loop function of the implanted device, and merely could serve as a secondary analysis module which provides the patient with a customized monitoring solution for evaluating the efficacy of the implanted device. Since internal function would not be affected, FDA approval would not be required for different types of monitoring schemes which would enable the central station to be alerted in a manner which is customized by the physician.

Cardiac Implementation of the ACS

A main utility of the ACS can be to alert patients to the occurrence of abnormal cardiac conditions meriting attention and intervention. In addition to providing an alert signal when a cardiac event has been detected, the ACS can serve primarily as a monitor that displays information related to sensed measures. For example, the implanted components can periodically send updates of a patient's "ischemia score" to an EXD. The ischemia score can be computed periodically (once a minute) and can be based upon ST-shift data for the patient. In the case when a patient exercises, the patient can view the readout of the EXD display 12a and monitor the ischemia score as it varies across the exercise session. The EXD can further be configured to issue an alert signal when the score increases above some amount, to provide the patient with trend graphs for the exercise session, and to compute rates of change and other parameters related to the ischemia score over time. The EXD can compute an index or probability that one or more abnormal cardiac conditions has occurred, and this measure can be computed using a statistically based criterion, self-norm data (e.g. previous exercise-related data) discriminant analysis, logistic regression analysis, neural network analysis, or other classification or discrimination scheme. In this case the patient can use some of their own judgment in monitoring the ischemia score or index in relation to their exercise program, their subjective experiences during exercise, and prior patterns they have viewed during prior exercise regimens.

While measures of ischemia may be based primarily upon electrocardiogram data collected from implanted electrodes, optical sensor data, pressure data, flow data, oxygenation data, sound data (e.g. cardio-sonogram), blood gas data, and other measures sensed by sensor which may be located both externally and internally may be used. Sensor data related to blood supply of selected cardiac vasculature (coronary arteries) may be combined or contrasted with the data from other vessels to detect regional or global changes in cardiac status. Data from at least two sensors which are indicative of the rate of blood flow, electrical response, or blood gas levels for at least 2 vessels of the heart can be used and differences or ratios can be computed (e.g. input/output function). Regardless of the sensors which are used, two or more sensors can be utilized in order to detect differential rather than absolute changes in sensed activity. In one preferred embodiment, implanted electrodes may be used to detect certain cardiac abnormalities, while at least two EKG electrodes are attached outside the patient in order to provide assessment of data, related to particular cardiac abnormalities, that might be invisible to the implanted electrodes. In other words, while implanted and intracardiac electrodes might be very useful in detecting certain cardiac abnormalities, external electrodes may provide for enhanced detection capability.

The recent historical record of cardiac activity may be used in order to adjust the criteria used to detect a medical event. The criteria may be adjusted based upon the rate at which a cardiac measure evolves and the duration of the persistence of a particular trait or pattern. Further the proportion of one type of event to another type of event, the size of and event, or the number of events over a selected time period may also server to alter the detection criteria, cardiac score, or alert which is sent to the patient. This may be important in tailoring detection to events that are relevant within a particular physiological context. For example, S-T elevation has been shown to be attenuated by prior occlusions or by protective medications (e.g., Cohen M V, Yang X M, Downey J M. Attenuation of S-T segment elevation during repetitive coronary occlusions truly reflects the protection of ischemic preconditioning and is not an epiphenomenon. Basic Res Cardiol. 1997 December; 92(6):426-34; Birincioglu M, Yang X M, Critz S D, Cohen M V, Downey J M S-T segment voltage during sequential coronary occlusions is an unreliable marker of preconditioning. Am J. Physiol. 1999 December; 277(6 Pt 2):H2435-41). Therefore, if a prior abnormal episode occurred in the recent past (e.g., within the last 5-10 minutes) then a subsequent episode may cause a diminished change (e.g. elevation) in the S-T interval. This may be in part due to the fact that recovery after occlusion may manifest in a slight S-T depression, which may counter a subsequent S-T elevation, although other mechanisms also play a role in this phenomena. The criteria for providing an alert may therefore be adjusted (e.g. decreased) after a first alert, or according to the historical record, in order to detect subsequent cardiac abnormalities which may be related to stenosis, but which may normally be rejected as adequate to be indicative of a meaningful cardiac abnormality. In one embodiment, the criteria used for detecting events are altered based upon at least one of: the elapsed time from a first detected event; the number of events within a recent period; and, the size of the events within a recent period.

Both direct and indirect measures of occlusion and cardiac status can be used by the implanted devices of the ACS. The use of the electrogram or electrocardiogram provide an indirect measure of stenosis by measuring the occurrence of hypoxia and ischemia in cardiac tissue. It may be advantageous to alternatively or additionally measure coronary arterial flow or blood oxygen saturation levels directly. Optical, sonic, flow, pressure, doppler, chemical, electrical (e.g., via impedence plethmograpy), and other sensors may be used to directly measure flow, gas levels, and input/output function of the cardiac vasculature. Chemical sensors can also be used to detect levels of biochemicals related to cardiac hypoxia. In the case of optical sensors, during acute ligation, ischemic myocardium with S-T elevation has been shown to become cyanotic and ischemic myocardium with S-T depression has been shown to be a normal red color (Ekmekci et al, 1961). An increase in discoloration towards a cyan-based spectrum can be detected by an optical probe, and may provide an indication of ischemia which anticipates or corroborates the occurrence of S-T elevation. Further, optical probes may be able to determine relative oxygen levels in arterial blood using near infra-red spectroscopy (NIRS) methods, which is a type of optically derived data.

NIRS data related to arterial oxygen saturation (SaO2), or other arterial gas estimations, can be evaluated in relation to measurements of oxygen and carbon dioxide levels made of transcutaneously or derived upon vessels themselves when sensors are implanted. Measures of systemic circulation (e.g., blood pressure or flowmetry) and oxygenation can be used in order to contextualize the cardiac SaO2 levels with respect to peripheral levels. The NIRS signal can be combined with other sensed data, and can be analyzed in a time-locked fashion, relative to cardiopulmonary events, such as components of the EKG signal. Statistical and signal analysis procedures such as template matching can be used to classify, score, or otherwise analyze the optical data. For example, the NIRS signal, or a transform of the NIRS signal, such as a frequency transform, can be analyzed over time using a principle component analysis (PCA) or independent component analysis (ICA) Further temporal, or temporal spatial (or frequency and phase for frequency transformed data) PCA can also be used to analyze and classify the incoming signals relative to a baseline period, or a period which is indicative or a symptom of the cardiac disorder to be treated or monitored. A number of measures and indices can be computed using NIRS. A tissue oxygen index (TOI) can be based upon measurements of oxyhemoglobin (HbO2), deoxyhemoglobin (Hb), and oxidized cytochrome oxidase (CtOx). It has been shown that the HbO2 and Hb measures are related directly to cellular activation. Increases in arterial blood volume (CBV) tend to follow the increase in HbO2 and in Hb, which summate to equal Total Hb (HbT). These are normally measured from an arbitrary zero, and the change is related to changes in blood volume. The conditions of the sensed NIRS signal can refer to the characteristics of the signal related to changes in these measures. The HbO2 and Hb measurements can be assessed independently, or can be used in an index which combines these measures in various manners. For example, HbO2 or Hb can be measured alone or HbO2+Hb can be assessed to provide HbT, or HbO2/(HbO2+Hb) can reflect relative oxygen utilization as a function of bloodflow, and Hbdiff ([HbO2-Hb]) is often used to track changes attributable to saturation alone. Small changes in HbO2 concentration can be reflective of blood flow, remembering that the accumulation of HbO2 in the cardiac tissue is dependent on both arterial inflow and venous outflow. Regional oxygen saturation (rSO2), may be derived from the ratio of HbO2 to total hemoglobin HbT, which is a percentage value of rSO2. NIRS methods can include diffuse optical imaging (DOI) techniques including diffuse optical tomography (DOT). Each optical sensor may have a source, or several sensors can absorb light from relatively distal source, the amount absorbed being related to activation of the regions between the source and sensor. The measured data can be used to produce cardiac or perfusion related time series data, which can be analyzed using both temporal and spectral techniques which are able to identify conditions of the signal and provide detection of abnormal cardiac conditions, such as those related to stenosis.

It is an object of the invention to provide sensors for sensing from two or more regions, and defining an abnormal episode only when the difference between these two regions is above a specified threshold. For example, the S-T deviation between a first bipolar montage may be compared to that of a second bipolar montage, and only when the difference in the S-T segment between the two montages, surpasses a criterion, is an abnormal episode detected, resulting in the generation of an alarm warning. The first and second montages may sense the electrocardiogram from different locations of the heart, and also in relation to different orientations of the electrical field. In other words, only certain montages may be useful in detecting certain types of abnormal activity which are "invisible" to other montages due to the orientation of the electrical field in relation to the sensors, and this differential detection can be used to classify, localize, and/or detect certain types of activity related to cardiac abnormalities. If the sensors are placed to sense from both arteries and veins, and input/output function can be created which is related to oxygen usage, and can also be utilized in a measure relevant to the hypoxic status of cardiac tissue, and indicative of an event such as stenosis.

Central-Station Methods and Strategies

The first section of this application has focused upon the CTI 500a and EXD 502a itself rather than what occurs when the alarms and data are transmitted to the central station. The next part of this application shall address how the data from the ACS is viewed and processed at this remote location. This includes how this information is evaluated by the medical practitioner who makes a decision about what type of intervention is needed based upon the data, and the patients record (e.g., patient's history, prescriptions for treatment etc).

As shown in FIG. 3, the EXD 502a can contain a specialized module 76f, which can be primarily realized in software or hardware, for automatically establishing an encrypted internet connection with a particular internet address. The module can contain information for logging into the remote server, sending identification and verification information, and then sending the alarm information and allowing for two way communication. The EXD 502a can also invoke an alarm response webpage (ARW) which contains a video screen with a number of components which are supplied by the central station. The ARW can contain for example, one or more screen portions with a video of the medical practitioner, their primary care physician, the physician at the nearest ER, a translator, and measures/raw data related to the alarm which has been triggered. The ARW is comprised of 'ARW components' which are supplied by the central station and which can be set by the base station service, or by other manner such as requested by the ARW protocol contained in ACS. The ARW which is viewed by the medical practitioner of the central station can be different than that which is displayed to the patient.

Figure 4:
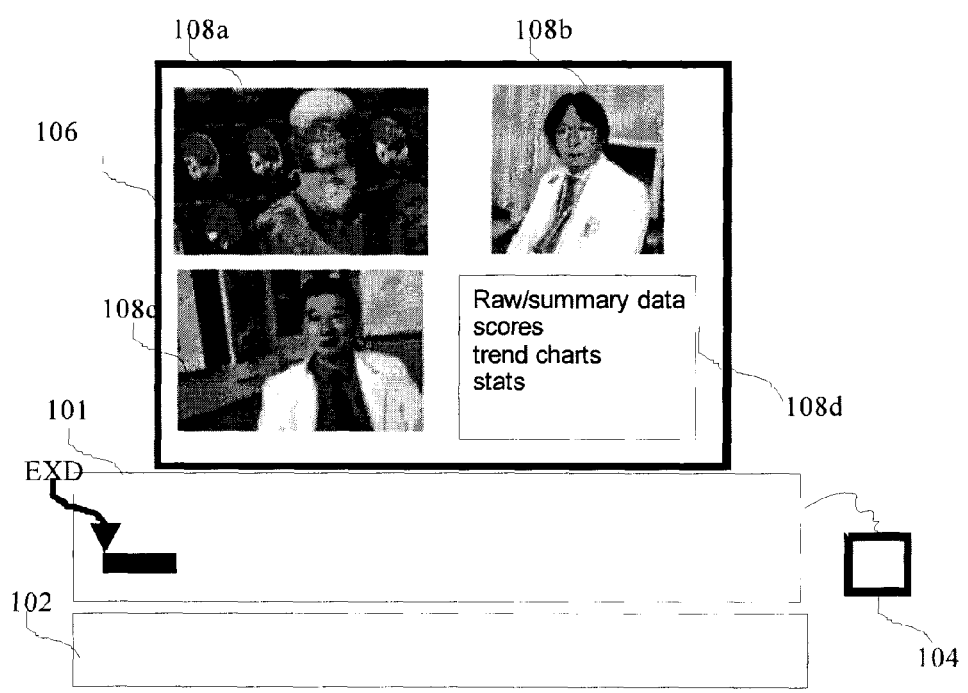
FIG. 4 illustrates customized web based program for communication with a central station and the ACS.

In FIG. 4, the screen of the ARW is shown, as displayed by a computer 101 to which the ACS has been plugged into and which can be any generic computer, or which can be a computer which has been configured to serve as a desktop version of the ACS. The ARW can also be displayed on the visual output source 12a of the ACS 10. The computer 101 has a keyboard 102 and a mouse 104 and a display terminal 106 which displays the ARW and its components. In one embodiment, the ARW can display multiple video images 108a,b,c which can be, for example, the medical practitioner at the central station, the patients primary physician, and a physician at the nearest emergency room to whom the patient may be sent. Alternatively, one of the video images can be of a medically certified translator who is located at the base-station or at a remote location. The ARW can also have a data sub-screen 108d which presents raw data, summary statistics, trends and alarm notices which have been generated by the ACS or the implanted ACS (IACS) system. The data sub-screen 108d can alternatively be a different sub-screen 108e which contains questionnaires that are presented to the patient in different languages, and these questionnaires and their multiple choice answers, can be viewed in the central-station in a different language. For example the questionnaires can be presented to the patient in English and to the medical practitioner in French. In the prior art neither the portable alarm systems, central stations, nor home based ACS systems utilize ARWs with customizable ARW components (i.e. subscreens) dedicated internet websites, or communication with servers in response to an alarm.

The ARW, along with the multimedia capacities and methods of the ACS such as those just described, offers very important advantages and may allow communication between the patient and the central station or physician to replace actual trips to the doctor's office for calibration, testing, adjustment, and other functions. The doctor can ask the patient to perform diagnostic activities at home, when an event is occurring (while this might not occur during an office visit). Using the ARW may also be used to review and discuss data quality, and other issues related to the working of the ACS.

Figure 5:
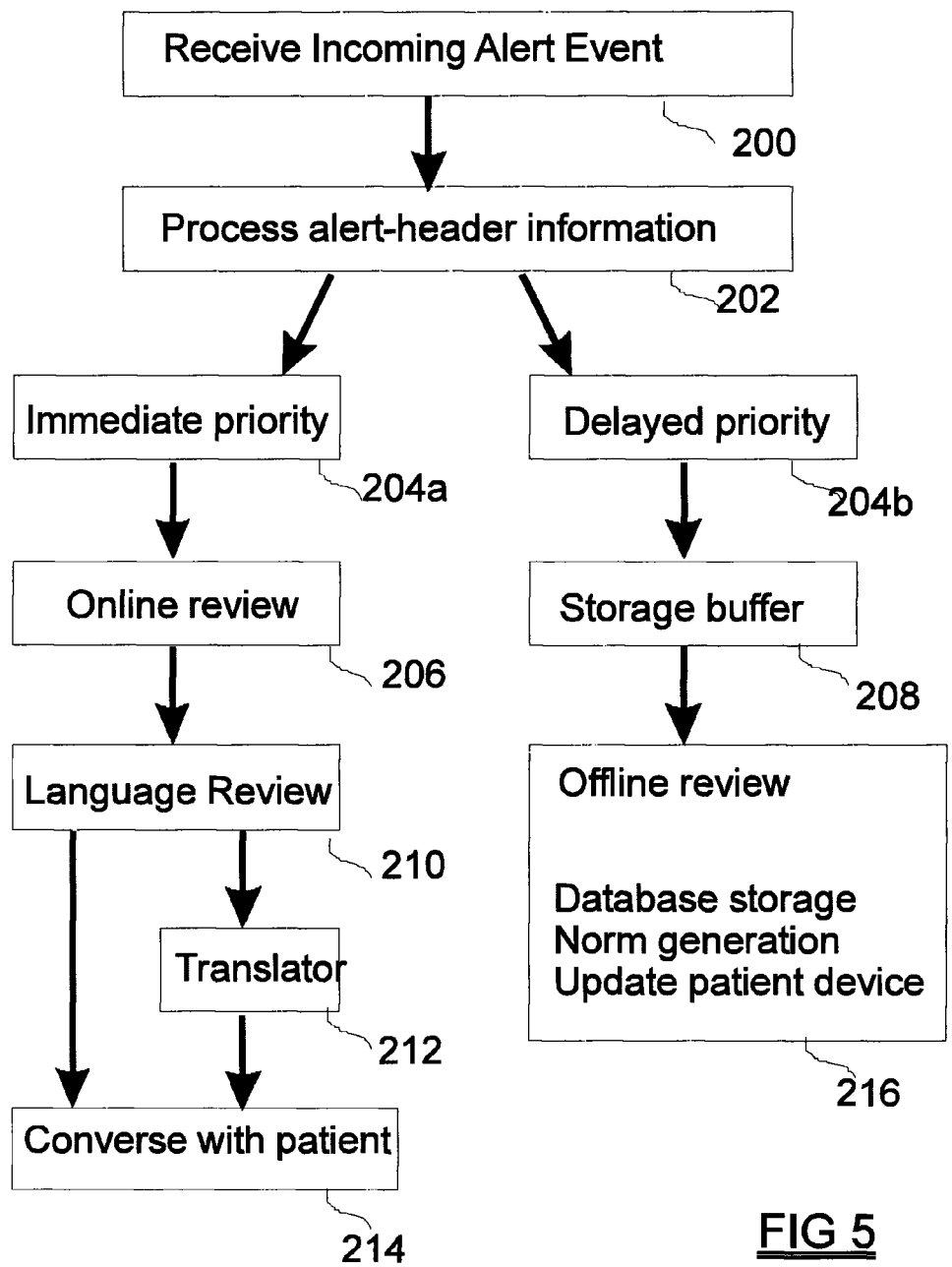
FIG. 5 illustrates a method of communication between a patient and the central station wherein data is processed according to event-tags that are sent with it.

FIG. 5 is a flow chart that shows a method of communication between a patient and the central station 505, wherein data is processed according to event-tags that are sent with it. All of the steps will be assumed to be implemented by a computer unless otherwise indicated. In block 200, the central station 505 receives an incoming alert event. In block 202, the central station 505 examines the alert-header information to determine the priority level of the alert. If the alert is an immediate priority alert, control is transferred to block 204a whereas lower priority alerts are processed by block 204b.

From block 204a, in which immediate priority alerts are processed, control is passed to block 206, which involves signaling to central station personnel that an immediate priority alert has occurred. Pertinent data sent from the EXD 502A is displayed on a computer screen in the central station, where appropriate personnel can immediately review/analyze the data. In block 210, the personnel will ascertain the most appropriate language to use to converse with the patient. If the medical personnel speak a different language then the patient, the services of a translator may be invoked, as indicated by block 212. The medical personnel then converse with the patient, either directly or through a translator, as indicated by block 214.

Delayed priority events, which are processed by block 204b, involve storing the data sent from the EXD 502A in a storage buffer, as indicated by block 208. This data may then be reviewed by central station personnel at a later time, as indicated by block 206. The data may be stored in a database. This data may be combined with previous data from that patient and possible with data from other patients to generate patient norm information, as previously described. In turn, these generated norms may be used to update the patient's EXD 502A, and possibly to update other patients' EXDs as well.

Central Station Analysis and Diagnosis

Once the data arrives at the central station the medical personnel must analyze these and make diagnostic decisions about treatment. While some of these decisions can be made based upon the pre-authorized prescriptions of the patient's primary care physician, some level of interpretation and judgment is also likely to be necessary in a port of the cases. The decision which will ultimately be made, will be relate to the training and experience of the medical practitioner. It is useful to have a number of automatic and cross-check methods for decreasing errors by the medical practitioner.

In one embodiment, not only the treatment prescriptions but also the data analysis and display screens are prescribed by the physician and customized according to a patient's disorder. The medical practitioner may be limited in the type of data analysis which is performed based upon the choices made by the primary physician. Additionally, the physician or medical practitioner can devise a set of criteria which automatically reject certain alarm data which is sent by the EXD 502a. Systems such as the CTI and EXD 502a are necessarily limited in their computational power. Accordingly the type of signal analysis and related evaluation algorithms provided in the CTI are severely limited. The EXD 502a may function to identify candidate events which cause alerts to be triggered, which its sends to the central station. These candidate alert events are then processed by a "false alarm processing stage" which can automatically reject certain alarms without requiring the attention of the medical practitioner, or can label the alarm data as "false alarm" prior to displaying this to the medical practitioner. Providing a multiple stage analysis procedure wherein one or more stages are constrained according the instructions of a primary care physician is an advantage of the invention and will lead to decreased numbers of false alarms and decrease the analysis requirements of the medical practitioners of the central station.

The central station can utilize a "patient montage" which is selected according to the patient being evaluated. The patient montage can contain analysis and trend programs that are set by the primary care physician or central station medical personnel in order to improve the analysis of patient data, since the analysis may be tailored to the individual patients. The patient montage can also provide the central station with questionnaires which are customized for each patient. These questionnaires can include the automatic provision of questions which may be timed. For example, 5 minutes after an alarm occurs, the questionnaire will prompts the central station medical practitioner to ask the patient a question, and this may be repeated at subsequent intervals, either as part of the medical record or in order to make treatment decisions.

According to the methods of the current invention the treatment decision made by the central station will different for any case which is determined to be a potential false alarm. In the case of data sent according to alarms which do not pass a "critical" criterion of a false alarm processing stage", or which are in any other way ambiguous, the treatment decision will be made based upon concurrence of the decision of the medical practitioner and at least 1 of the following:
 a. the treatment decision of a second medical practitioner.
 b. the treatment decision of an automated data analysis module.
 c. the treatment decision of the primary care physician.

When option 'a' is used then the first and second medical practitioner should be blind to the decision of the other, prior to the joint evaluation of the data. If option 'b' is selected, then the automated data analysis can provide a binary decision or probability score. This may be based upon a comparison of the alarm data with reference data which may include self-norms of the patient, population norms, disease state templates, factor, scores, and classifying schemes such as discriminant analysis, where either a normal or abnormal score is generated, or both are generated and must differ by some amount in order for an objective decision to be made (70% abnormal likelihood; 30% normal likelihood). If option 'c' is used then the final decision can be made according to the policy of the central-station where the physician's decision trumps the decision of the medical practitioner, or where agreement by both is needed for certain treatment decisions to be made. Different methods of analysis will be detailed more fully in the section entitled "data analysis".

In the ACS, when an alarm (or event or alert) is triggered a "post-alarm" protocol can be activated which causes these systems to handle new information differently than in their other modes. The central-station can also function in a default mode, and this mode is altered by the type of alarm which is sent. For example, when the central-station receives an alarm it may (automatically) begin to do at least one of the following according to a post-alarm protocol which can be different for different alarms:
 1. continuously store data sent by the ACS
 2. relay data sent from the ACS to the receiving ER
 3. send an e-mail, page, automated call, or other alarm to the primary physician.

The ACS, EXD, and central station systems and methods described offer a number of innovative features which can greatly increase the medical benefit derived by the patient.

What is claimed is:

1. A medical system for providing a medical alert in response to the occurrence of a medical event comprising:
 a patient implanted device for monitoring a patient's condition, detecting medically relevant events, and sending data to an external device upon detection of medically relevant events, said data including an alert signal;
 a receiver that receives data pertaining to the patient's condition;
 an alert module for receiving the alert signal issued by said_implanted device, said alert module for receiving said alert signal and issuing the alert signal to a central station through a first communications network or a second communications network, wherein the alert module is controlled by a processor;
 a transmitter operatively coupled to the alert module;
 a patient alerting device operatively coupled to the alert module;
 the alert module being configured to attempt to establish communication with a central station through the transmitter according to a primary communications protocol through said first communications network when the alert signal is generated, and wherein the alert module further determines whether attempts to establish communication with the central station according to the primary communications protocol have failed within a predetermined time interval according to specified failure criteria and to further take remedial action in response to such failure, said patient alerting device being activated to take remedial action upon failure of the first communication protocol;
 wherein the remedial action activates the patient alerting device to indicate that the primary communications protocol has failed through said first communications network, and attempts to establish communication with the central station through the transmitter according to at least one secondary communications protocol through said second communications network.

2. The medical system of claim 1 wherein a specified failure criteria comprises failure to communicate within an interval defined by a wait parameter signal, said wait parameter signal selected from a programmable contingency based upon a type of data being communicated, the urgency of the data being communicated, or a fixed input to said alert module.

3. The medical system of claim 1 wherein the secondary communication protocol provides communication using at least one of: the internet, WIFI, Bluetooth, a phone, and a cell phone, and this occurs using at least one of:
 automatic methods; and
 with the assistance of the patient.

4. The medical system of claim 1 wherein the at least one secondary communication protocol includes two or more alternative communication protocols chosen in a particular order, the order being defined according to at least one of: according to a user preference, and, according to a set preference, and these are invoked automatically when the primary protocol fails.

5. The medical system of claim 1 wherein the primary protocol establishes communication using a local access number and the secondary protocol uses a nationwide "1-800" number to establish communication.

6. The medical system of claim 1 wherein the primary protocol establishes communication with a central station service and the secondary protocol establishes communication with a primary care physician service.

7. The medical system of claim 1 wherein the primary protocol establishes communication with a primary care physician service and the secondary protocol establishes communication with a central station service.

8. A medical system for providing a medical alert in response to the occurrence of a medical event comprising:
 a patient implanted device for monitoring a patient's medical condition, and sending data to an external device, said data including a plurality of alert signal types;
 a receiver that receives the data;
 an alert module that reviews the data to determine whether to issue a predetermined type of alert signal through a first communications network or a second communications network, wherein the alert module is controlled by a processor;
a transmitter operatively coupled to the alert module;
a patient alerting device operatively coupled to the alert module;
wherein the alert module is configured to attempt a primary alert protocol through said first communications network if the alert module determines that an alert signal of a predetermined type should be generated, and that alert module is_further configured to determine whether attempts to provide the predetermined type of alert signal according to the primary alert protocol have failed according to specified failure criteria and to take remedial action in response to such failure;
wherein the remedial action includes activating the patient alerting device to indicate that the primary communications protocol has failed, and attempts to provide the predetermined type of alert signal using at least one secondary alert protocol through said second communications network.

9. The medical system of claim 8 wherein the first alert signal establishes communication between an external patient controller and a central monitoring station.

10. The medical system of claim 8 wherein the at least one secondary alarm protocol is selected to be at least one of two or more alternative alarm signals which may be chosen in at least one of: a particular order; and, according to a user preference, and these occur automatically when the primary alarm protocol fails.

11. The medical system of claim 8 wherein the primary alarm protocol provides an alert signal using a local access number and the secondary alert signal uses a nationwide "1-800" number.

12. The medical system of claim 8 wherein the primary alarm protocol establishes alarms a central station service and the secondary protocol alarms a primary care physician service.

13. A medical device for providing a medical alert in response to the occurrence of a medical event comprising:
a patient implanted device for monitoring a patients condition_detecting medically relevant events and sending data to an external device upon_detection of medically relevant events;
a receiver that receives data pertaining to a patient's condition;
an alert module that reviews the data to determine whether to issue a predetermined type of alert signal to a central station through a first communications network or a second communications network, wherein the alert module is controlled by a processor;
a transmitter operatively coupled to the alert module;
a patient alerting device operatively coupled to the alert module;
the alert module being configured to attempt to establish communication with a central station through the transmitter according to at least one of (1) a primary communications protocol through said first communications network, and (2) at least one secondary communications protocol through said second communications network, said communications protocol being selected based upon the type of alert that is generated by the alert module.

14. The medical system of claim 13 wherein the steps which occur due to a failure of communication of a protocol differ depending upon which communication protocol is selected.

15. The medical system of claim 13 wherein a failure of communication of a protocol only results in alerting of a patient if the alert is related to one of a set of selected medical event types.

* * * * *